US00PP09697P

United States Patent [19]

Johnston

[11] Patent Number: Plant 9,697

[45] Date of Patent: Nov. 19, 1996

[54] *ACER PALMATUM* NAMED 'BENI SHI EN'

[76] Inventor: Harold Johnston, 31 Ware Rd., Tallassee, Ala. 36078

[21] Appl. No.: 599,420

[22] Filed: Jan. 16, 1996

[51] Int. Cl.[6] ..... A01H 5/00

[52] U.S. Cl. ..... Plt./53.6

[58] Field of Search ..... Plt./53.6

*Primary Examiner*—James R. Feyrer

[57] ABSTRACT

A new and distinct *Acer palmatum* (Japanese Maple) tree discovered as a seedling within progeny resulting from a collection of bulked seeds, taken from several varieties within the species, which is distinguished particularly by its characteristic varied expression of leaf shapes, leaf sizes and coloration. The new tree 'Beni Shi En' is further characterized by forming a tree with an uncommonly dense canopy for the botanical class and by forming a small to medium sized tree at maturity, which has a weakly dominant central leader, formed by numerous slightly ascending scaffold branches, or subject to pruning, can be formed into a specimen with a rounded to broad vase-shape. Foliage coloration of this tree will vary widely as a function of location of culture, but which normally express, variably, a reddish to red-purple blush over a medium green matte top surface which has darker green striation or botches, and a clear, darker green color on the glabrous bottom surface.

6 Drawing Sheets

BACKGROUND OF THE NEW TREE

A favored and valued market class of trees within the landscape and nursery industry is the Japanese Maple. Within this market class is a widely diverse variation of trees, having differences in leaf form, leaf color, canopy density, bark color and texture, and vigor. The outstanding characteristics of these usually include unique leaf forms, alluring leaf colors, and wide ranges of vigor, or combined traits allowing for the maintenance of specimen size over a long period of time without having to heavily prune such specimens with great frequency. Many of the plants within this class of trees may be easily maintained at a small size to fit into a small space, and take on an enhanced character with advancing age, while offering interesting and attractive colors and forms which can be widely applied in appointing a garden landscape. This market class is dominated by the species *Acer palmatum*, which the skilled artisan respects for the diversity of expression mentioned above.

The tree of this invention was discovered by me as a single, conspicuously unusual plant within a population of seedlings from specimen trees of several varieties of *A. palmatum*, which I had collected and planted. The seedling was immediately noticeable due to its deep red coloration and white variegated streaks, when compared with the remaining seedlings of the block, and by its unusually but consistent, nonuniform leaf size and shape characteristics. Upon recognition of the notable differences of this seedling, I took steps to retain it for further observation and testing. The new tree was first asexually reproduced by me at my production location in Tallassee, Ala., by grafting and has since been repeatedly so reproduced through a series of generation on seedling *Acer palmatum* root stock. In observing the clonal progeny, I have determined that the novel and distinctive traits of this new *A. palmatum* tree, 'Beni Shi En' are firmly fixed, true to type, and virtually identical to those of the originally selected tree in every respect.

SUMMARY OF THE INVENTION

The tree of this invention, which I have denominated 'Ben Shi En', is novel and distinct within the species *A. palmatum*, by the following combination of highly unusual but desired characteristics:

Forming a variety of deeply incised, or deeply cut leaves, having sinus angles which may be sufficiently narrow to allow the laminas of the lobes to overlap or which may be uncommonly wide for the species;

Having leaves which may contain from about three to about seven fully developed lobes of essentially lanceolate shape, and frequently containing one or more lobes which have stopped growing as an initial or grown to an under-developed stage;

Having leaves which are matter, medium green, and shaded with a brownish to reddish blush overcolor of varying intensity, which may appear in dapples along the lamina, but which is normally most intensive at the apex of the lobes and minute, deeper green striations;

Having leaves with bottom surfaces which are glabrous and more glabrous than the top surface which is highly unusual for trees within the species; and, Having leaves which are of a wide range in both size and character of lobes which, while of widely differing lengths, often curved and overlapping, normally are symmetrical and have sharply, doubly serrated margins.

Taking the above characteristics with the ability of this tree to form a small, strong specimen, with an exceedingly dense canopy, this tree will be a valuable addition to this increasingly popular market class of available landscape trees.

DESCRIPTION OF THE ILLUSTRATIONS

The novel characteristics of new Japanese Maple 'Beni Shi En' are depicted in the accompanying drawing figures which show, in turn:

FIG. 1, which shows a six year old specimen which has attained a height of about six feet and a span of about three fett, shows the shape of the tree trained to a rounded profile, the color of the bark and the density and character of the canopy of the tree.

FIG. 2, which shows the bark of a six year old specimen.

FIG. 3, which depicts the upper surface, characteristics of the cut of the sinuses, the coloration, margin and venation of the leaves, the leaf petioles.

FIG. 4, which shows a grouping of leaves with a range of fall colors from yellow to bright red and again illustrates the variability in the form, size, shape and texture of the leaves.

Figure 2:
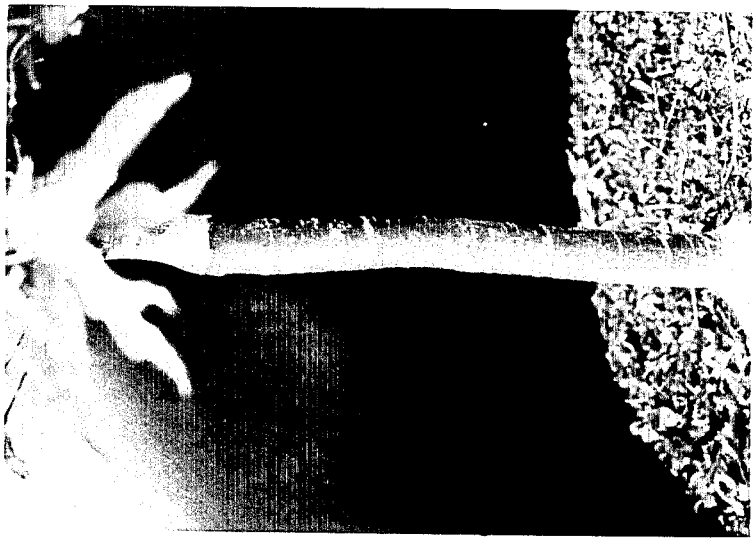
Figure 1:
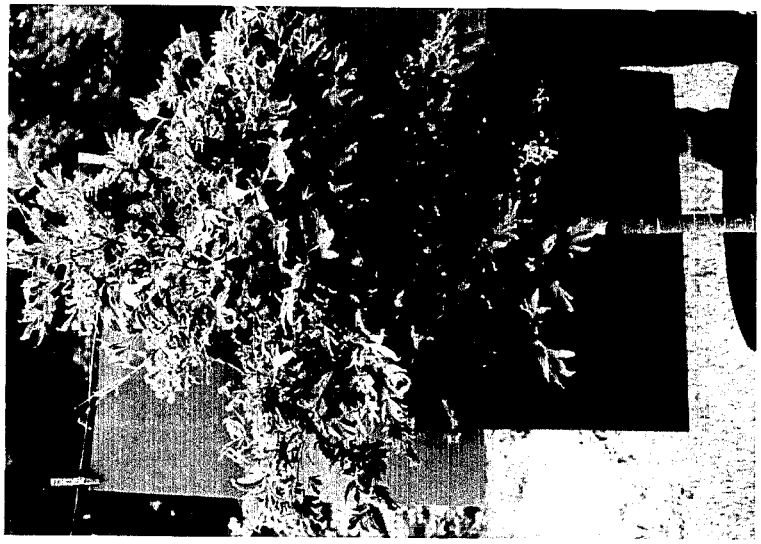
Figure 3:
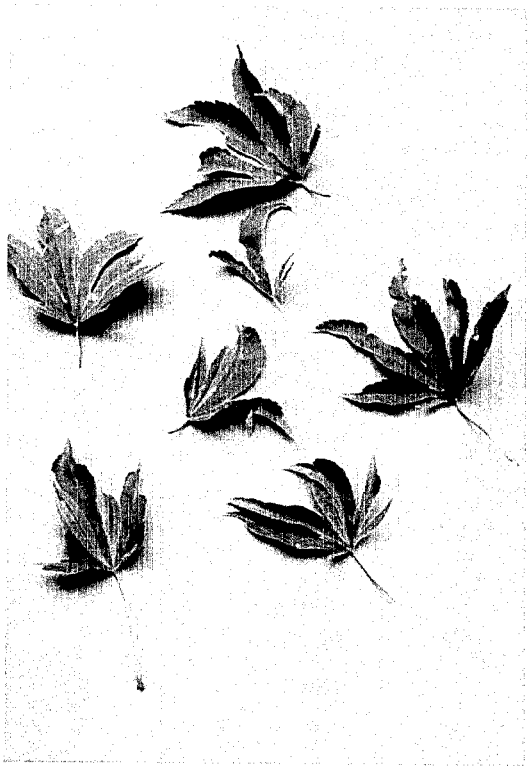
Figure 4:
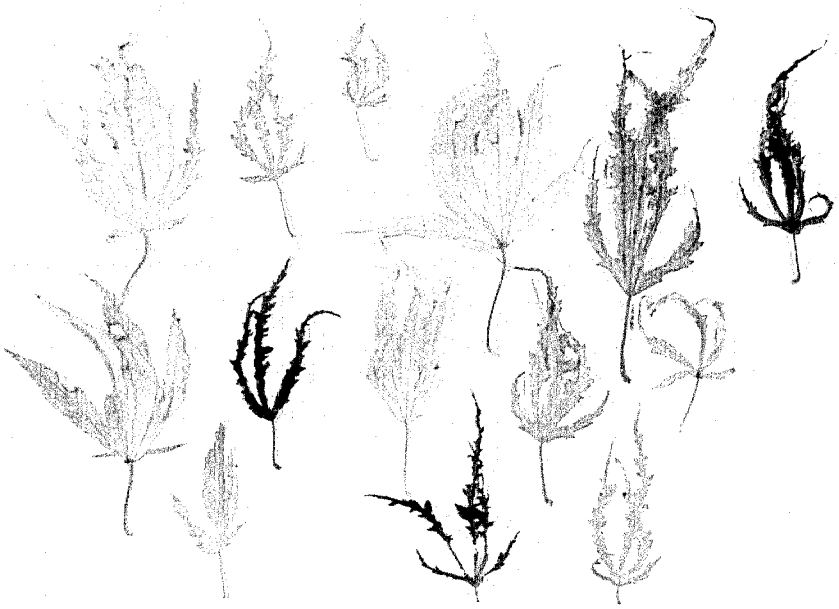
Figure 5:
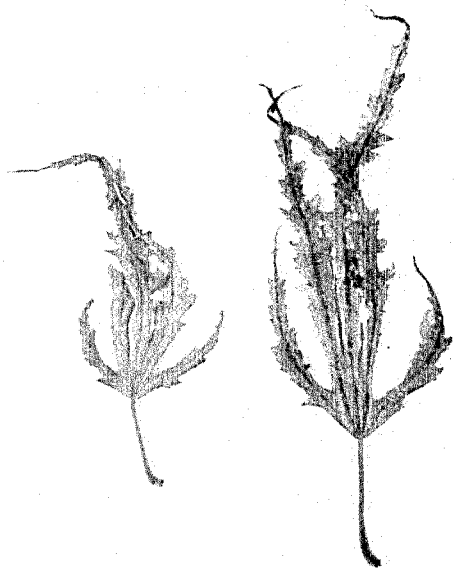
FIG. 5, shows the bright red leaves as described in the color section using The Royal Horticulture Society Color Chart.
Figure 6:
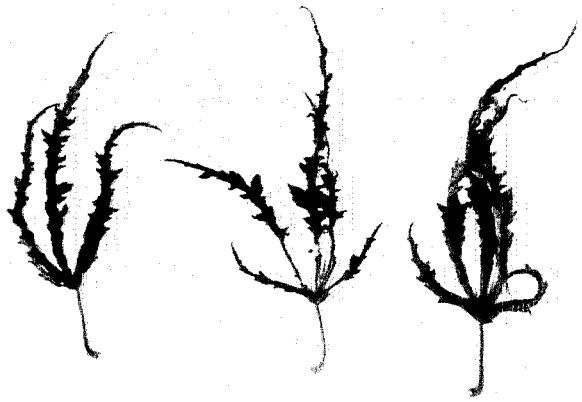
FIG. 6, shows the burgundy leaves as described in the color section using The Royal Horticulture Society Color Chart.
Figure 7:
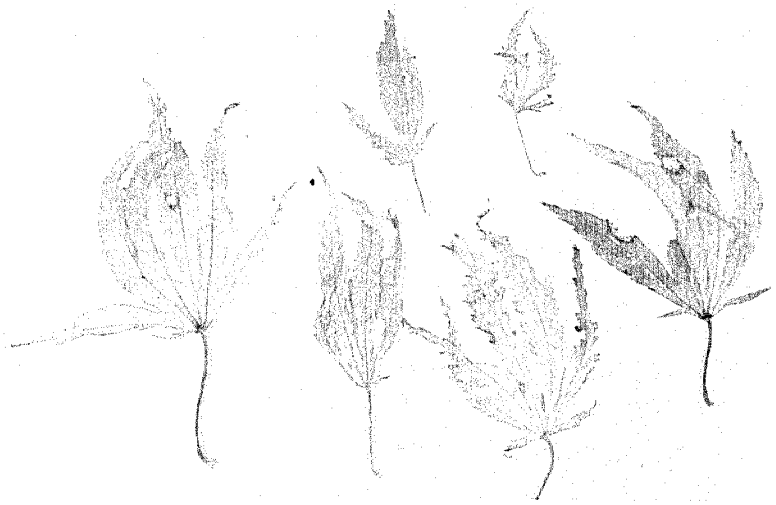
FIG. 7, shows the yellow to brown leaves as described in the color section using The Royal Horticulture Society Color Chart.

The combined photographic figures show one unique characteristic of this tree, which is that the leaf form is consistently inconsistent. Every leaf appears different in shape.

DESCRIPTION OF THE NEW TREE

The following is a detailed description of my new female Japanese maple based upon observations of a tree growing in the Johnny's Pleasure Plants Nursery for the past 9 years. The observations have been made over a period of time since 1984. The color designations being used throughout this specification are based on the Munsell Color System derived from electronic evaluation using a Minolta Spectrophotometer CM 2002.

Origin: Seedling selection from a population of *A. palmatum* seeds of mixed, bulked origin collected from a variety of trees of the species.

Parentage: Unknown. The originally observed sport from a seedling originated in a bed of seedling *A. palmatum*. The original seeds for this bed resulted from the open pollination of a number of Japanese maples.

Classification:

*Botanic.*—*Acer palmatum.*

*Commercial.*—Japanese maple.

FORM

Small deciduous tree of rounded to vase shaped, dense, slightly ascending (may become pendulous with increased length of several years growth) habit with a prolific branching character.

HEIGHT

In a period of 8 to 9 years, grafted scions of the new plant have reached an average height of 6 to 7 feet with a trunk size of 2 to 3 inches. The growth rate is vigorous and normally about 1 to 2 feet per year.

The tree maintains a dense and slightly pendulous habit and exhibits very abundant branch development. The foliage is fine textured, and exhibits little to no pubescence.

BRANCHING

The branching is abundant with branches diverging at an angle of approximately 45 to 60 degrees from the central trunk. The wide angles of these scaffold branches increase the strength of the crotches formed. Also, the wide angle to upswept branches create a rounded to vase shaped canopy, with the leaves drooping to form a layered appearance.

FOLIAGE

The leaves are opposite, simple and range from 2 to 8 cm long and 2 to 8 cm wide. The leaves have 3 to 7 lobes, deeply dissected with each lobe being extremely variable in size and shape. Individual lobes range from 1 cm to 7 cm long and 1 mm to 1.5 cm wide. Lobes are lance shaped to lance-oblong shaped with doubly serrated to tattered appearing margins which are recurved to straight. Lobes of the leaves range from slightly coarser than the fine texture of 'Koto no ito' to a finer texture than a coarser textured 'Matsu kaze'. Leaves are inconsistently variegated from red or purple-red on the lobe margins fading to green in the middle to yellow green midvein. Flecks and streaks of red, purple, white, green and yellow give the marbled appearance which is reflected in the name. Bottoms of leaves are glabrous and a dull to glossy green. Leaves have a weeping or drooping habit. Petioles are 1.5 to 3 cm long. Fall foliage color is a bright gold, red, burgundy, and brown. In California, leaves maintain a deep purple color through the summer. In the South, the foliage changes to purple and green.

COLOR

According to Munsell Color System, upper leaf surfaces of mature leaves have a hue ranging from 8.5 y to 6.86 yr, value of 3.4 and chroma of 2.0. The back surfaces have a hue of 5.0 gy, value of 4.2 and a chroma of 2.9. Fall color according to The R.H.S. Color Chart and illustrated in 4 of the attached photographs range from RH1C (yellow) to RH183A (burgundy) to RH166B (brown) to RH44B (bright red). The bark of Beni Shi En at 4 years old is RH146C (yellow-green).

STEMS

Young stems, between one and two years old, are about 2 to 4 mm diameter and range in color from green to purple with spots of yellow or yellow-green at the nodes or petioles.

BUDS

Buds are valvate and about 1 to 2 mm in length. They are red-brown in color. In general, the outstanding characteristics of this new cultivar of *A. palmatum* 'Beni Shi En' is its unique, non-uniform foliar characteristics which distinguish it from all other cultivars of Japanese maples.

This new *A. palmatum* is easy to graft in summer or winter using a side veneer graft which provides commercial appeal and assures trueness-to-type. The tree has an excellent growth rate under normal fertilizer and moisture conditions and offers exceptional leaf characteristics and stability of these characteristics which assures it position in the commercial landscape and collectors pallet of plants for selection.

I claim:

1. The new and distinct cultivar of *Acer palmatum*, 'Beni Shi En' substantially as herein shown and described, characterized by a unique marbled foliage with a fine textured appearance and a rounded to vase shaped and slightly pendulous growth habit and its dense foliage of fine textured variegated leaves.

* * * * *